(12) United States Patent
Pedrazzini (10) Patent No.: US 10,597,229 B2
(45) Date of Patent: Mar. 24, 2020

(54) STACKER CRANE WITH AN IMPROVED SLIDING MECHANISM

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 198 days.

(21) Appl. No.: 15/532,107

(22) PCT Filed: Dec. 1, 2015

(86) PCT No.: PCT/IB2015/059240
§ 371 (c)(1),
(2) Date: Jun. 1, 2017

(87) PCT Pub. No.: WO2016/088032
PCT Pub. Date: Jun. 9, 2016

(65) Prior Publication Data
US 2017/0267451 A1 Sep. 21, 2017

(30) Foreign Application Priority Data

Dec. 3, 2014 (IT) .............................. MI2014A2075

(51) Int. Cl.
*B65G 1/04* (2006.01)
*B66F 9/14* (2006.01)
*G01N 35/04* (2006.01)
*B66F 9/07* (2006.01)

(52) U.S. Cl.
CPC .............. *B65G 1/0414* (2013.01); *B66F 9/07* (2013.01); *B66F 9/072* (2013.01); *B66F 9/141* (2013.01); *G01N 35/04* (2013.01); *G01N 2035/0425* (2013.01)

(58) Field of Classification Search
CPC ... B65G 1/0414; B65G 1/0407; B65G 1/0435
See application file for complete search history.

(56) References Cited

U.S. PATENT DOCUMENTS

| 2009/0136331 | A1 | 5/2009 | Muser | |
|---|---|---|---|---|
| 2016/0016732 | A1* | 1/2016 | Koide | H04B 10/80 414/273 |
| 2017/0008701 | A1* | 1/2017 | Terrill | B65G 1/0492 |

FOREIGN PATENT DOCUMENTS

AT      505 757 A4      4/2009

* cited by examiner

*Primary Examiner* — Saul Rodriguez
*Assistant Examiner* — Willie Berry, Jr.
(74) *Attorney, Agent, or Firm* — Jacobson Holman, PLLC.

(57) ABSTRACT

The present invention relates to a stacker crane (2) for transporting, inserting and picking containers of biological material test tubes in/from locations (3) of a plurality of shelves (4) of a warehouse (1) for storing containers of biological material test tubes. The stacker crane (2) is able to move the containers of biological material test tubes in the three Cartesian directions x, y and z, so as to reach the locations (3), wherein the stacker (2) comprises a first carriage (21) and a second carriage (22) able to slide independently of, and to be released from, the first carriage (21) in direction y.

11 Claims, 9 Drawing Sheets

STACKER CRANE WITH AN IMPROVED SLIDING MECHANISM

BACKGROUND OF THE INVENTION

The present invention relates to a stacker crane with an improved sliding mechanism and to a storage for storing containers of biological material test tubes provided with said stacker crane.

Stacker cranes, also more simply referred to as stackers, are now employed in the most various fields of industrial automation for the automated transport of different types of materials inside large warehouses, as well as for inserting and/or picking material from specific locations of shelves, often significantly high off the ground.

The sliding movement of the movable structure of the stacker in known solutions is promoted, in particular in movements along direction y, by the presence of wheels, which adequately accompany the movement of the movable structure along the tracks.

Problems appear with a sliding movement of this type since a lack of accuracy and/or instability can occur in certain cases. This can be due for example to the presence of frictions during the sliding movement, various imbalances caused by the progressive wearing out of the wheels over time, impurities depositing on the wheels or still again to the possibility of an unscrewing at the fastenings between the movable structure and wheels.

All malfunctions can have serious consequences such as the stacker stoppage during the sliding movement thereof or a coming out of the wheels from the tracks, promoted by the fact that there is a given clearance during the translation along the tracks. The latter drawback can naturally result in the transported material falling or even the stacker overturning.

The risks described above occur in even greater measure the higher the stacker is, or if it is designed to transport particularly heavy materials or materials sensitive to overturning.

Patent Application AT505757 A4 describes a stacker crane for loading and unloading a rack from locations of a shelf, provided with a telescopic extension. In particular, the telescopic extension comprises a first telescopic section connected to the stacker crane and a second telescopic section connected to the first telescopic section. Such a solution therefore allows the rack to move easily during the loading and unloading operations from the locations, but involves a significant mechanical stress when the load is cantilevered moved by means of the aforesaid telescopic extension. The mechanical stress is only partly reduced by means of the use of suitable support rollers, which reduce the bending moment loaded on the second portion of the telescopic extension, to the detriment of the stress on the first section of the extension.

With particular reference to the field of laboratory automation plants designed to move test tubes containing biological material samples, there is an increasingly stronger need to arrange conveniently cooled storages inside the plant. Such storages allow the biological samples analyzed to be stored for a longer or shorter time so that they are available again to the plant as needed for a repetition of the analyses by modules connected to the automation. The need for increasingly more storage space therefore requires the use of increasingly voluminous storages and the necessary application of suitable movement systems, for example of the type corresponding to the aforesaid stacker cranes, thus also adding the problems disclosed above connected with movement to the complexities of the storing systems themselves.

BRIEF DESCRIPTION OF THE INVENTION

It is the object of the present invention to provide a stacker crane with an improved sliding mechanism without the problems disclosed above, and in particular provided with increased stability and accuracy, less exposed to wear, frictions and to mechanical stresses of any type, and therefore without any risk of the material transported falling or overturning. Particular attention is to be paid to the sliding aspect of the stacker along the two coplanar directions x and y.

It is a further object of the present invention to provide an apparatus for storing and retrieving large volumes of test tubes in/from large storages, which ensures increased storing/retrieving dynamism (throughput) while ensuring a stable, accurate movement of the containers with reduced wear.

This and other objects are achieved by a stacker crane for transporting, inserting and picking containers of biological material test tubes in/from locations of a plurality of shelves of a storage for storing the containers of biological material test tubes, the stacker crane is able to move the containers of biological material in the three Cartesian directions x, y and z, so as to reach the locations, and comprises:

first guide means along direction x, comprising a first pair of guides;
second guide means along direction y, orthogonal to direction x, comprising at least a second pair of guides;
a movable structure comprising a first carriage and a second carriage, the first carriage is able to slide integrally with the second carriage in direction x and along the first pair of guides;
the second pair of guides is separate and independent from the first carriage and from the second carriage,
the first carriage is integrally provided with a third pair of guides for the second carriage, which contribute to form the second guide means when said first carriage is arranged at the second pair of guides, thus aligning the third pair of guides to the second pair of guides, and
to each of the first carriage and second carriage is integrally connected at least one pair of sliding mechanisms positioned along the respective ends, the second carriage is able to slide independently of and to be released from the first carriage along the second guide means in direction y, by the translational movement of the sliding mechanisms of the second carriage from the third pair of guides to the second pair of guides and vice versa.

Thereby, the interaction between the second pair of guides and the third pair of guides allows an increased stability and accuracy of the movements to be obtained, thus minimizing the frictions and mechanical stresses during the independent movement of the second carriage. Moreover, the possibility of independently moving the first and the second carriage allows to obtain a lightening of the load to be translated and subsequently, less wear and mechanical stress.

The term direction x in the present invention means the sliding direction along an axis in a plane of a group of planes parallel to the support plane of the stacker crane.

The term direction y in the present invention means the sliding direction along an axis in a plane of a group of planes parallel to the support plane of the stacker crane and orthogonal to direction x.

The term direction z in the present invention means the sliding direction along an axis in a plane of a group of planes perpendicular to the support plane of the stacker crane and orthogonal to direction x and to direction y.

In a further aspect, the aforesaid objects are achieved by a storage for storing containers of biological material test tubes comprising a plurality of shelves defining a plurality of locations for the containers of biological material test tubes, in which the storage comprises a stacker crane for transporting, inserting and picking containers of biological material test tubes in/from locations of the plurality of shelves according to the present invention.

BRIEF DESCRIPTION OF THE DRAWINGS

These and other features of the present invention will become more apparent from the following detailed description of suitable embodiments, where a preferred embodiment is disclosed by way of a non-limiting example in the accompanying drawings, in which.

DETAILED DESCRIPTION OF THE INVENTION

Figure 1:
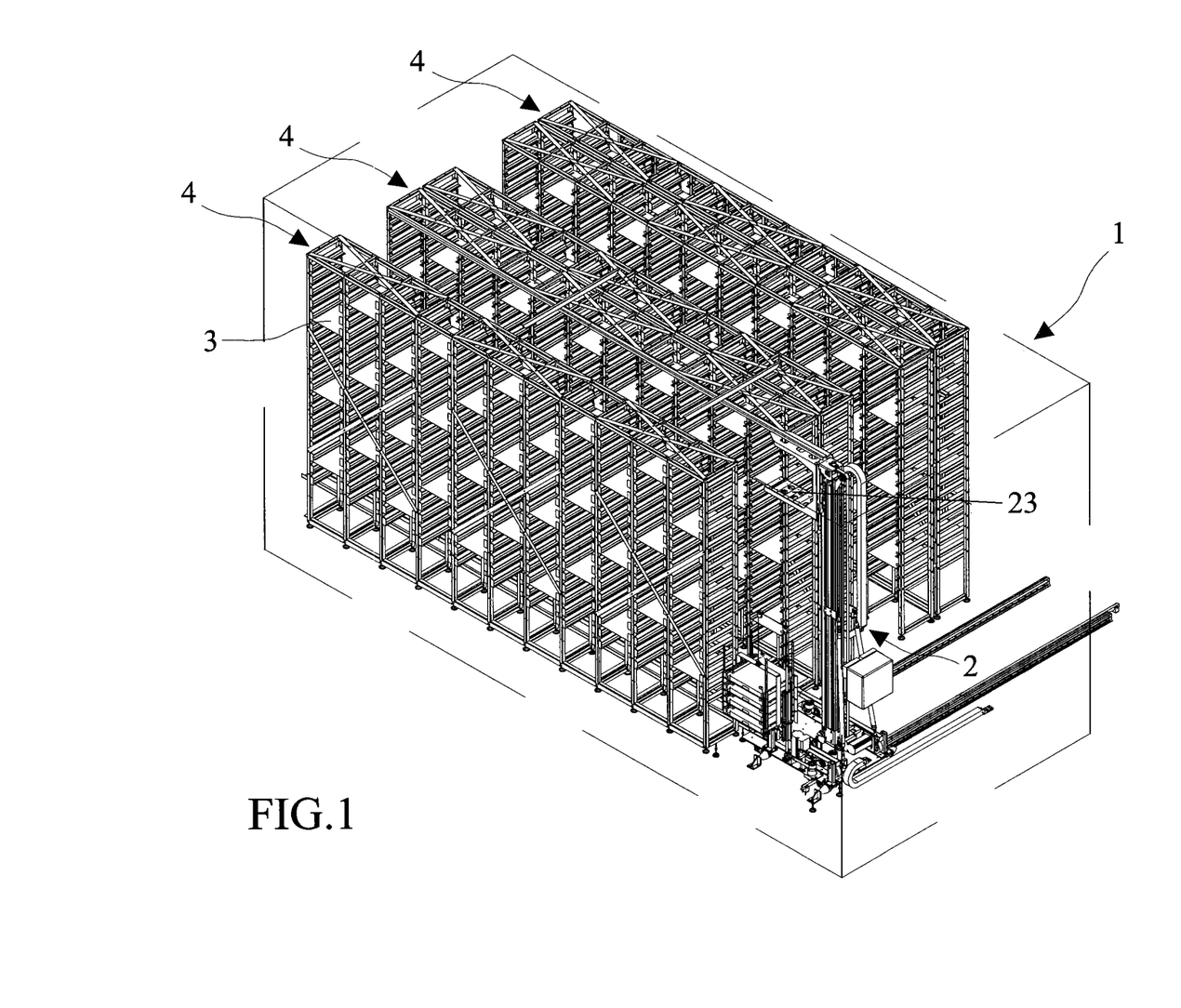
FIG. 1 shows a perspective view of a storage for storing containers of biological material test tubes provided with a stacker according to the present invention, for storing and retrieving said containers.

FIG. 1 shows a storage 1 for storing material, in particular containers of biological material test tubes, comprising a stacker crane 2, or hereinafter stacker, designed to transport containers of the aforesaid material and to insert and pick them in/from locations 3 of a plurality of shelves 4 of the storage 1. The stacker crane 2 is able to conveniently move the containers of biological material test tubes in the three Cartesian directions x, y and z, so as to reach the locations 3. In particular, the stacker 2 is capable of first being positioned at the feet of the suitable shelf 4, then rising along the vertical so as to reach the suitable height, in front of the specific location 3 to be reached.

In the embodiment herein disclosed, with particular reference to FIG. 1, the storage 1 comprises a plurality of shelves 4 facing each other, which define suitable lanes for the movement of stacker 2 between two shelves 4 facing each other. Moreover, the shelves 4 are arranged so as to define a further lane for the movement of the stacker 2 at the ends of the plurality of shelves 4. The aforesaid lanes are described in greater detail below.

With reference to the Cartesian set of three directions x, y and z, in the present embodiment direction x is relative to the direction of movement of the stacker 2 along the lane at the ends of the plurality of shelves 4, defined below as end lane or middle lane. Direction y is relative to the direction of movement of the stacker crane 2 along the lanes between two shelves 4 facing each other, defined below as intermediate lane, thus obtaining the translation of the stacker 2 between a succession of locations 3 arranged on a same plane parallel to the support plane of the aforesaid stacker 2, or row of locations 3. Direction z is relative to the direction of movement of the stacker 2 along a succession of locations 3 arranged on a same plane perpendicular to the support plane of the aforesaid stacker 2, or column of locations 3.

The following disclosure does not change, whatever the material transported by the stacker 2, nor does the container in which such material is housed; this detail is therefore omitted below, as it is not relevant.

Figure 2:
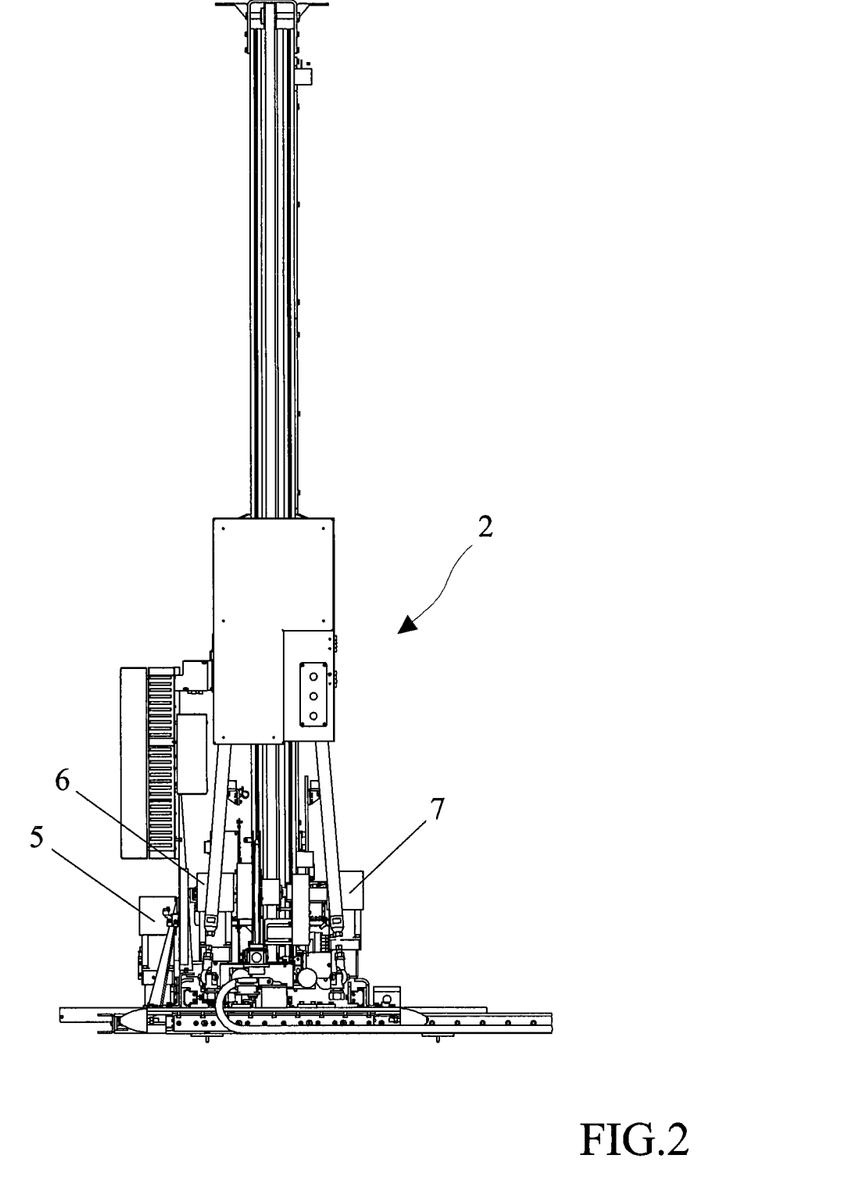
FIG. 2 shows a side view of the stacker according to the present invention.

In the embodiment disclosed in the accompanying figures, the movement in all directions of the stacker 2 is driven by suitable motors 5, 6 and 7, each of which designed to move the stacker 2 along one of the directions x, y and z (FIG. 2). In alternative embodiments (not disclosed), the movement along the directions x, y and z can also be obtained by a single motor equipped with a drive system able to transfer the motion in each one of the desired directions.

Figure 3:
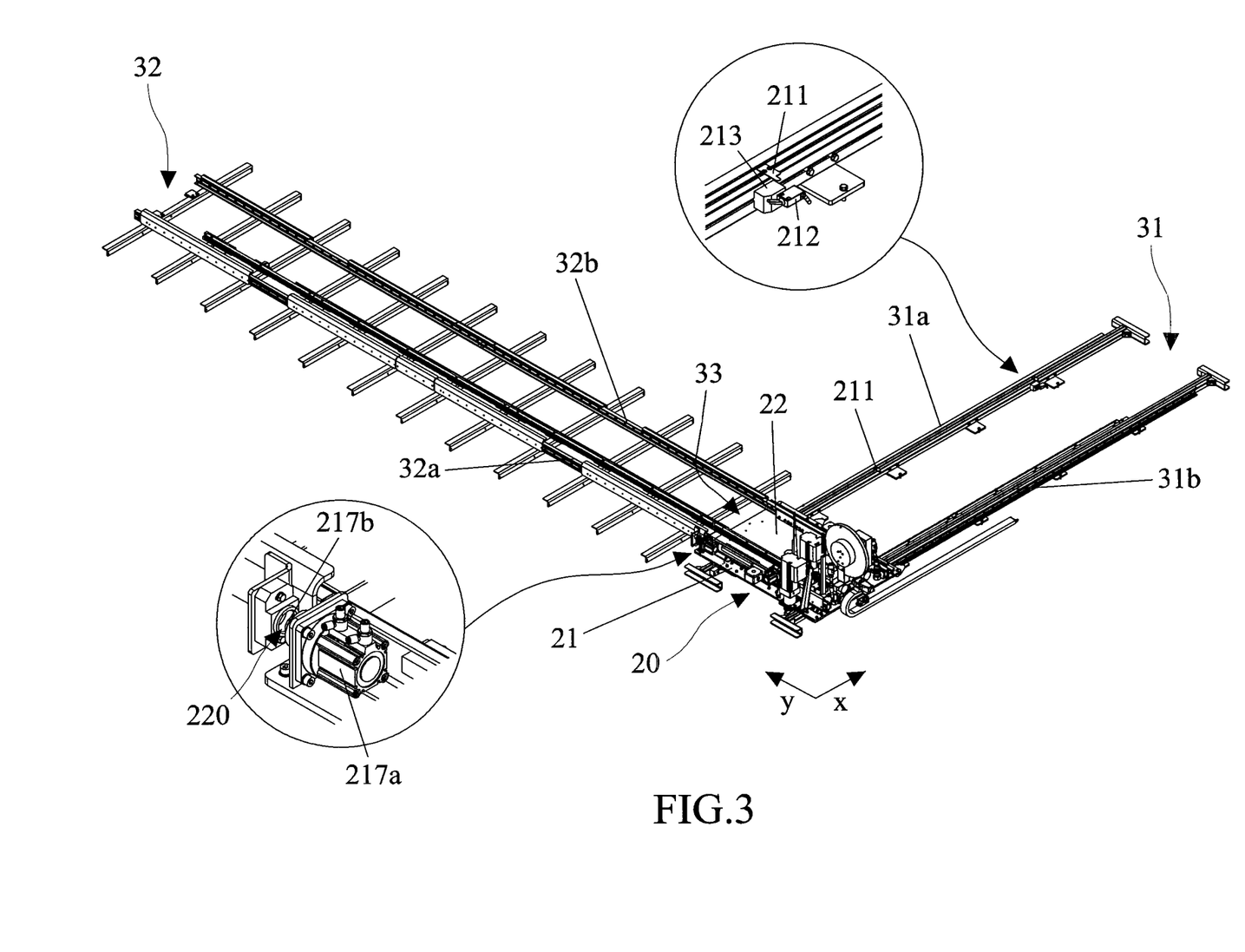
FIG. 3 depicts a perspective view of the movable structure of the stacker and guide means along which it slides, with two details relative to the locking means and to the stroke-end sensors, respectively.

The movement of the stacker 2 in the two directions x and y, which are perpendicular to each other, aimed at positioning in front of the suitable column of a shelf 4 and in anticipation of the subsequent arrangement at the specific location 3 belonging to the same column, is promoted by the presence of a movable structure 20 comprising a first carriage 21 and by a second carriage 22 (FIG. 3). The second carriage 22 can move integrally with the first carriage 21, in a position above it, or can be detached therefrom and can move independently, as will become apparent below. The movable structure 20 further comprises a third carriage 23 (FIG. 1) able to move integrally with the first carriage 21 and to the second carriage 22, or independently from each of the aforesaid carriages, as will become apparent below.

The stacker crane 2 comprises first guide means 31 along direction x, comprising a first pair of guides 31a, 31b, and second guide means 32 along direction y, orthogonal to direction x and comprising at least a second pair of guides 32a, 32b. Moreover, stacker 2 comprises third guide means along direction z.

In the embodiment herein disclosed, in particular, the first guide means 31 comprise a single first pair of guides 31a, 31b. The second guide means 32 instead comprise a plurality of second pairs of guides 32a, 32b, in particular two in number, arranged parallel side by side, so that each second pair of guides 32a, 32b is arranged between two of the pluralities of shelves 4 facing each other, defining the intermediate lanes. Moreover, the first pair of guides 31a, 31b of the first guide means 31 is arranged at the same end of the plurality of the second pairs of guides 32a, 32b, thereby defining the end lane. The third guide means for the third carriage 23 are instead defined by a belt drive system.

In a further embodiment (not shown), the first guide means comprise a single first pair of guides, as described above for the shown embodiment, and the second guide means comprise a plurality of second pairs of guides arranged aligned and at the opposite ends of the first pair of guides, so that each second pair of guides is at a plurality of shelves, said shelves being placed side by side and separated by the first pair of guides. In an embodiment of the aforesaid type, the first pair of guides defines a middle lane while the pluralities of second pairs of guides define the intermediate lanes.

In order to allow the lightening the load even during the movement of the stacker 2 along direction x, the aforesaid second pair of guides 32a, 32b, whether it being single or greater in number, is separate and independent from the first carriage 21 and from the second carriage 22. Moreover, the first carriage 21 is integrally provided with a third pair of guides 33a, 33b for the second carriage 22, which contribute to form the second guide means 32 when the first carriage 21 is arranged at the second pair of guides 32a, 32b, thus aligning the third pair of guides 33a, 33b to the second pair of guides 32a, 32b.

The integral movement of the two carriages 21, 22 occurs during the movement of the stacker 2 in direction x, in which the first carriage 21 is able to slide integrally with the second carriage 22 in direction x along the first pair of guides 31a, 31b. The movement of the second carriage 22 along direction y occurs along one of the second pairs of guides 32a, 32b, and of the third pair of guides 33a, 33b, said third pair of guides 33a, 33b being integral with the first carriage 21, as shown by way of example in FIG. 3. The second carriage 22 is able to slide independently of, and to be released from, the first carriage 21 along the second guide means 32 in direction y, from the third pair of guides 33a, 33b to the second pair of guides 32a, 32b and vice versa, by means of the use of suitable sliding mechanisms 40 of the second carriage 22 described in greater detail below. The third carriage 23 is able to slide integrally with the first carriage 21 and the second carriage 22 in direction x along the first pair of guides 31a, 31b, integrally only with the second carriage 22 in direction y along the second pair of guides 32a, 32b and independently along the third guide means in direction z, thus being released from the first carriage 21 and from the second carriage 22.

Figure 4:
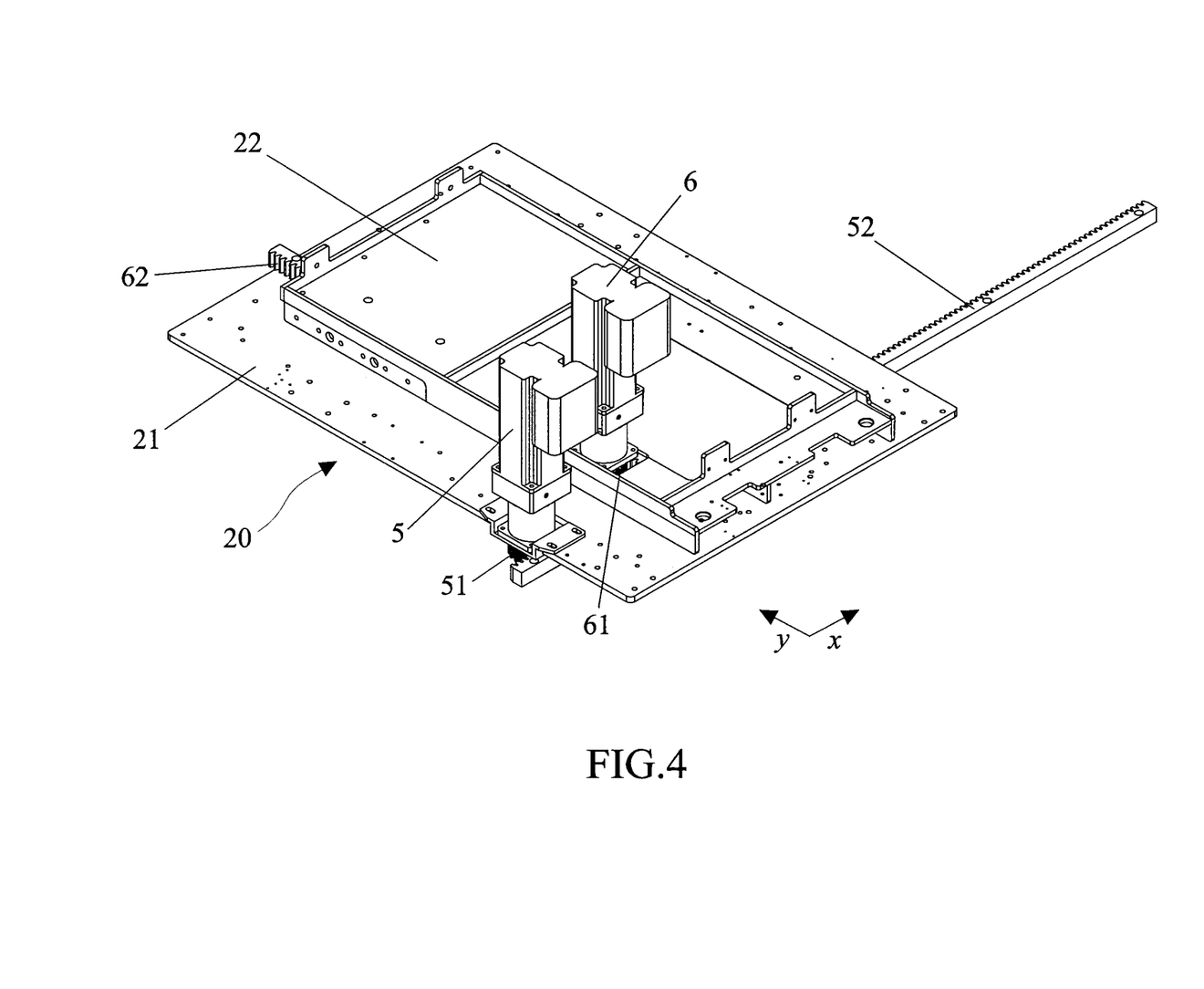
FIG. 4 shows a perspective view of the first and of the second carriage of the movable structure of the stacker.

Due to the action of a first motor 5 on a first pinion-rack pair 51, 52 (FIG. 4), the stacker 2 first moves in direction x along the first pair of guides 31a, 31b. In this step, the whole movable structure 20, therefore with the carriages 21, 22 and 23 integral with each other, moves in the direction indicated by arrow x in FIG. 3 until it engages one of the brackets 211 (FIGS. 3, 5) with a sensor 210 integral with the first carriage 21 (FIG. 5), which sensor 210 discriminates against reaching a given intermediate lane along direction y. The stacker 2 is then designed to move into said intermediate lane, while uncoupling the second carriage 22, and consequently the third carriage 23, from the first carriage 21.

Figure 5:
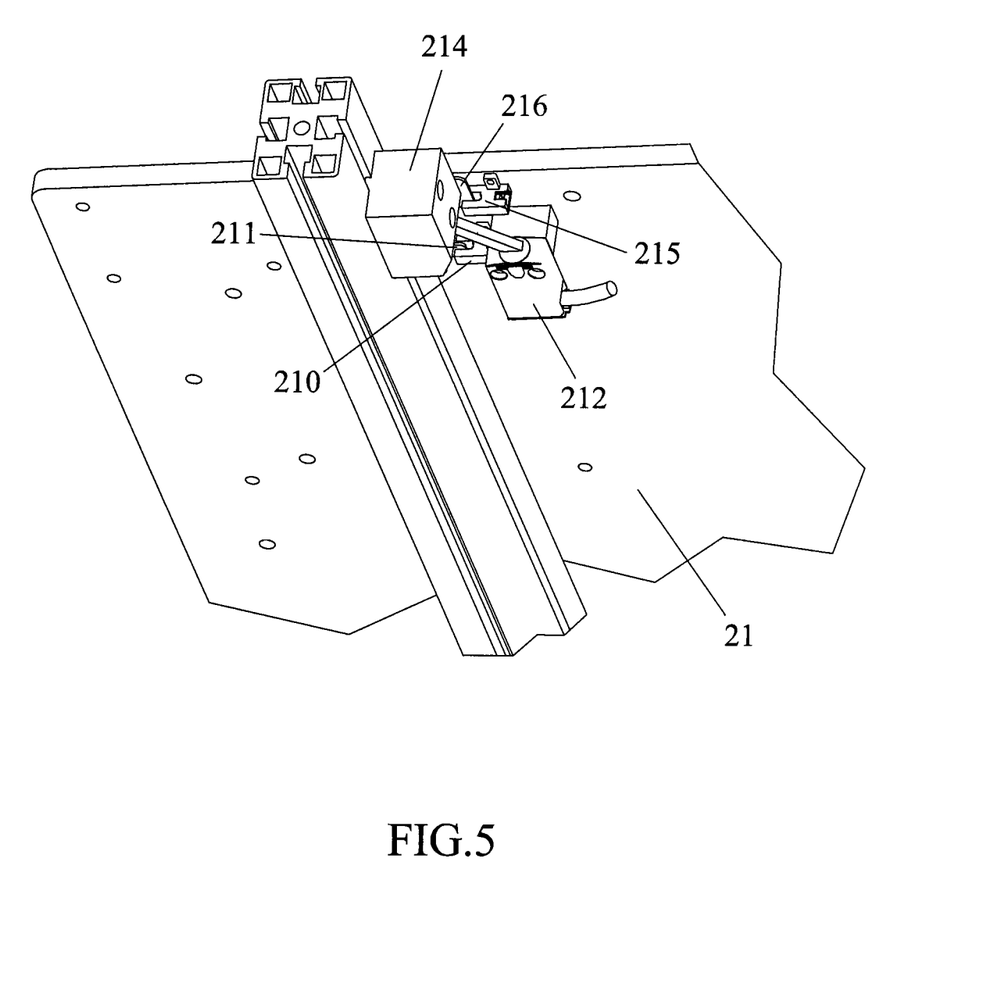
FIG. 5 depicts a perspective view from the bottom of certain sensors integral with the first carriage of the movable structure.

Moreover, a stroke-end sensor 212, again integral with the first carriage 21, discriminates against the same from reaching the two end positions in the movement thereof, by engaging two separate blocks 213 and 214 positioned in the aforesaid end positions shown in FIG. 3 (in which the end-stroke sensor 212 is shown for convenience in a position which is isolated from the first carriage 21 while actually not being isolated therefrom) and in FIG. 5, respectively. In this last drawing a further sensor 215 is shown, which is also integral with the first carriage 21, and which engages a further bracket 216 in the end-stroke position shown therein.

The first carriage 21 and the second pair of guides 32a, 32b are provided with a first locking mechanism able to ensure the alignment of the movable structure 20 with the second pair of guides 32a, 32b. In particular, said locking mechanism comprises a cylinder 217a integral with the first carriage 21 and a housing 220 integral with a member of the second pair of guides 32a, 32b. Moreover, the first carriage 21 and the second carriage 22 are provided with a second locking mechanism able to ensure the connection of the first carriage 21 with the second carriage 22. In particular, said second locking mechanism comprises a cylinder 218a integral with the first carriage 21 and a housing 221 integral with the second carriage 22. In the same way, a third locking mechanism, similar to the second locking mechanism, can be provided for coupling and uncoupling the second carriage 22 and the third carriage 23.

As mentioned, when the movable structure 20 has reached the suitable intermediate lane along which it is necessary for the stacker 2 to move in direction y, cylinder 217a (FIG. 3), still integral with the first carriage 21, is activated, such cylinder 217a moves a pin 217b which is inserted in the suitable housing 220 integral with one of the members of the second pair of guides 32a, 32b, so as to ensure the optimal alignment of the movable structure 20 with the second pair of guides 32a, 32b in view of the sliding movement of the stacker 2.

Then the sliding movement of the second carriage 22 in direction y along the second pair of guides 32a, 32b (FIG. 3) is performed, driven by the action of a second motor 6 on a second pinion-rack pair 61, 62 (FIG. 4) and calibrated by the encoder of the second motor 6 itself (therefore without the need for any sensor). Such a sliding movement can occur up to positioning the second carriage 22, which is provided with the third carriage 23, at the lowest location 3 of the shelf 4 (FIG. 1) in front of which the stacker 2 must then rise to pick/insert the material which it is designed to transport. The sliding movement along direction z is therefore performed by the third carriage 23, which is able to slide independently in direction z along the third guide means, which are defined by a belt system in the present embodiment, thus being released both from the first carriage 21 and from the second carriage 22.

At the end of the upward movement of the stacker 2, i.e. of the third carriage 23, the second carriage 22 returns, by moving in the opposite direction along the second pair of guides 32a, 32b, toward the first carriage 21 to achieve the connection therebetween.

Figure 6:
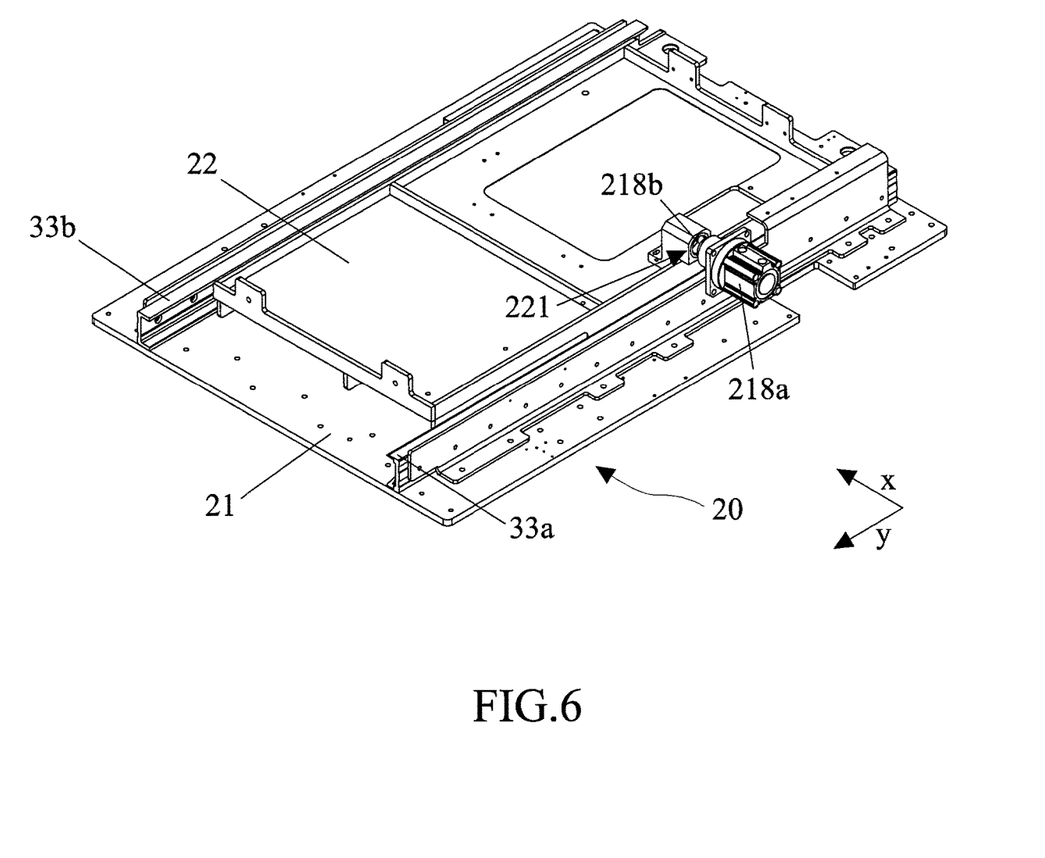
FIG. 6 shows a perspective view of the movable structure, with a locking mechanism of the second carriage on the first carriage.

The coupling of the second carriage 22 with the first carriage 21 is ensured by the second locking mechanism, i.e. the cylinder 218a integral with the first carriage 21 moves a pin 218b which engages the suitable housing 221 integral with the second carriage 22 so as to ensure the connection between the two carriages 21 and 22 (FIG. 6). In the same way, the third locking mechanism (not shown), similar to the previous one, can ensure locking and releasing of the third carriage 23 with respect to the second carriage 22 when the movement occurs along direction y and consequently, with respect to the first carriage 21 when the movement occurs along direction x.

Thus the movement of the stacker 2 continues, possibly moving again along direction x and then in another lane along direction y.

Figure 7:
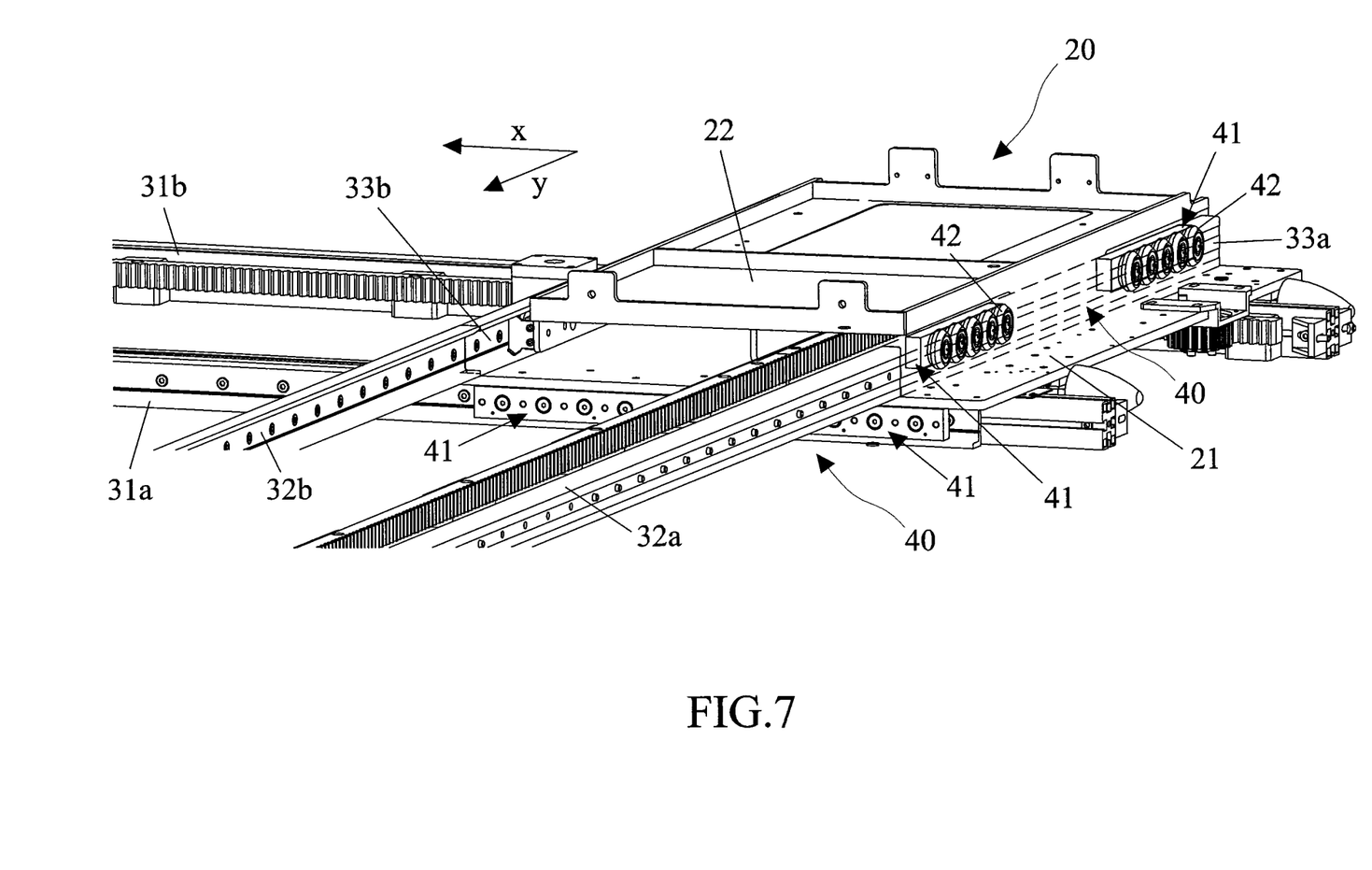
FIG. 7 shows a perspective view of the movable structure of the stacker provided with sliding mechanisms.

In relation to both the sliding operations examined, i.e. the one of the first carriage 21 along the first pair of guides 31 and the one of the second carriage 22 along the second pair of guides 32, they occur smoothly due to the presence of at least one pair of sliding mechanisms 40 which are connected integrally to each of the two carriages 21, 22 (FIG. 7).

Two sliding mechanisms 40 located along the ends in width of the carriages 21, 22 are indeed connected to the two carriages 21, 22 themselves in order to be integral therewith (FIG. 7 shows a single sliding mechanism 40 for each carriage).

Figure 9:
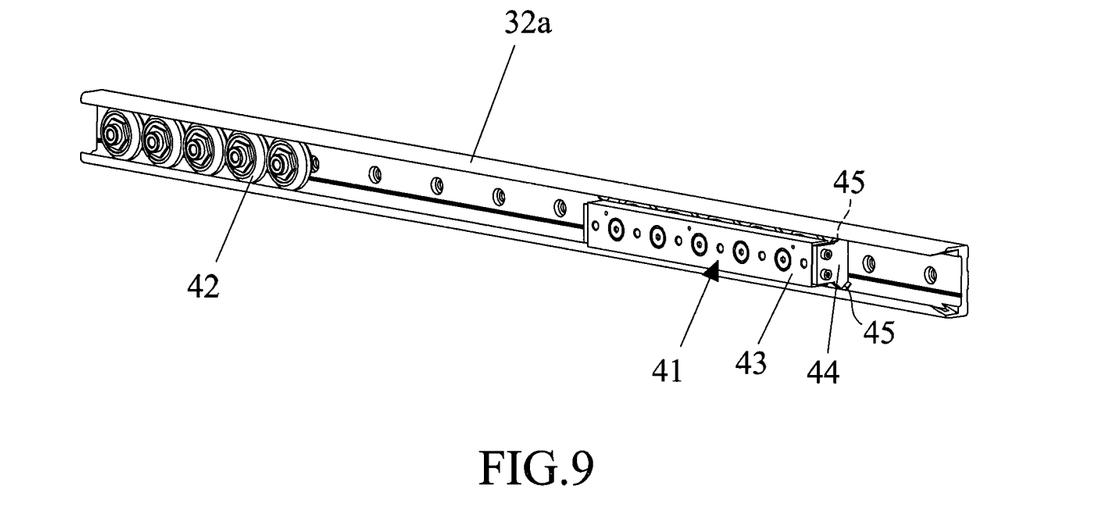
FIG. 9 depicts a detailed perspective view of the sliding mechanism.

As clearly shown in FIG. 9, every sliding mechanism 40 has one or more sliders 41 able to slide inside the first 31a, 31b, second 32a, 32b and third 33a, 33b pairs of guides, according to the carriage to which they are coupled. Each of the sliding mechanisms 40 provides a coupling plate 43 to each of the respective carriages 21, 22, which supports suitable rolling means able to transform the sliding friction of the translational movement into rolling friction. In the embodiment disclosed herein, such rolling means comprise a series of bearings 42 sliding inside the respective first 31a, 31b, second 32a, 32b and third 33a, 33b pairs of guides. In the same way, it is possible to use cylinders, wheels or further members able to facilitate the movement while limiting the impact from friction.

Figure 8:
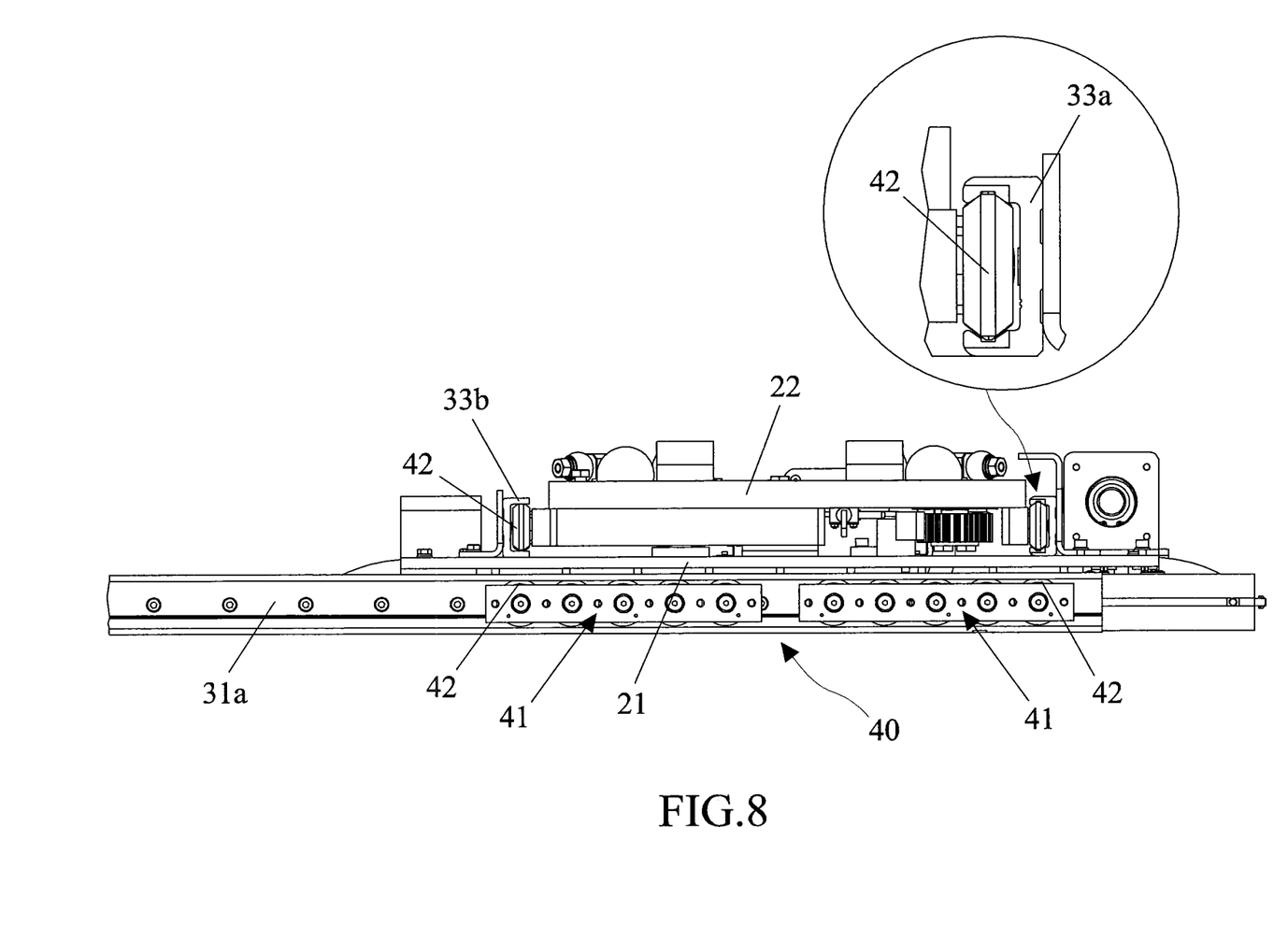
FIG. 8 shows a side view of the movable structure of the stacker and of the sliding mechanism, with a detail relative to the shape of the pair of guides provided on the first carriage.

End members 44 are coupled to the edges of the plate 43 and, along with the first 31a, 31b, second 32a, 32b and third 33a, 33b pair of guides, close a containment space of the rolling means, i.e. bearings 42, so as to prevent impurities from entering (FIGS. 8 and 9; in the latter, left-hand side slider 41 is not shown to better show the bearings 42 therein). In particular, the first 31a, 31b, second 32a, 32b and third 33a, 33b pairs of guides are made with a "C"-shaped profile, so as to allow an improved definition of the containment space and a controlled sliding of the sliding mechanisms 40. Indeed, the end members 44 are coupled to the edges of the coupling plate 43 which, along with the "C"-shaped profile of the respective pairs of guides 31a, 31b, 32a, 32b, 33a, 33b, close the containment space. The profile of the pairs of guides can in any case be realized with sections different from the "C"-shaped profile, e.g. "U"-shaped or with more complex shapes, in any case suitable to allow the closing of a containment space of the sliding mechanisms.

It is worth noting how the end members 44 are shaped so as to enter the profile, preferably "C"-shaped, of the first 31a, 31b, second 32a, 32b and third 33a, 33b pairs of guides, with flaps 45 thus accurately closing said containment space of the rolling means, i.e. of the bearings 42.

The dimensions of the sliders 41 are perfectly suitable for the "C"-shaped profile of the guides 31a, 31b, 32a, 32b; in light of such an adjustment, there is absolutely no clearance in the sliding movement of the sliders 41 in the guides, and this is reflected in a perfectly stable and accurate movement of the two carriages 21, 22 and accordingly of the stacker 2. Moreover, when the second carriage 22 separates from the first carriage 21 to move in an intermediate lane along direction y, the second pair of guides 32a, 32b and the third pair of guides 33a, 33b, along which the second carriage 22 is to slide, are perfectly aligned due to the action of the cylinder 217a (FIG. 3); thereby, the sliders 41 of the second carriage 22 can adequately slide along the aforesaid second 32a, 32b and third 33a, 33b pairs of guides.

The innovative aspect of the invention is therefore given by the fact that the sliding movement of the carriages 21, 22 of the stacker 2 along the first 31 and the second 32 guide means ensures, with respect to known solutions, less friction and an increased stability and accuracy in the movement of the stacker 2 with respect to known solutions. This results in the elimination of all risks of overturning, or even just of unbalancing, of the stacker 2, and therefore of falling down of the transported material.

The compactness of the movable structure 20 of the stacker 2 along the vertical direction (and therefore in height) is particularly significant. With due contrivances, this allows to reach even locations 3 of shelves 4 which are positioned lower down or higher up with respect to the known solutions.

The mechanism described is also significantly quieter than the existing solutions in which the sliding movement occurs due to wheels, and moreover undoubtedly shows increased resilience as compared thereto.

Finally, the possible assembly of the guides with the "C"-shaped profile of the guides facing outward promotes easier maintenance, when required.

The invention thus conceived is susceptible to several modifications and variations, all falling within the scope of the invention concept.

In practice, any materials as well as any shapes and dimensions may be used, depending on the needs.

The invention claimed is:

1. A stacker crane for transporting, inserting and picking containers of biological material test tubes in/from locations of a plurality of shelves of a storage for storing said containers of biological material test tubes, said stacker crane is able to move said containers of biological material test tubes in the three Cartesian directions x, y and z, so as to reach said locations, and comprises:
   first guide means along said direction x, comprising a first pair of guides;
   second guide means along said direction y, orthogonal to said direction x, comprising at least a second pair of guides;
   a movable structure comprising a first carriage and a second carriage, said first carriage is able to slide integrally with said second carriage in said direction x along said first pair of guides;
   wherein said second pair of guides is separate and independent from said first carriage and from said second carriage,
   said first carriage is integrally provided with a third pair of guides for said second carriage, which contribute to form said second guide means when said first carriage is arranged at said second pair of guides, thus aligning said third pair of guides to said second pair of guides,
   to each of said first carriage and second carriage is integrally connected at least one pair of sliding mechanisms located along the respective ends, and
   said second carriage is able to slide independently of, and to be released from, said first carriage along said second guide means in said direction y, by the translational movement of said sliding mechanisms of said second carriage from said third pair of guides to said second pair of guides and vice versa;
   wherein said sliding mechanisms comprise one or more sliders able to slide inside said first, second and third pairs of guides; and
   wherein said sliding mechanisms comprise a coupling plate, to be attached to said first carriage and second carriage respectively, which supports rolling means able to slide inside said first, second and third pairs of guides and to transform the sliding friction of said sliding movement into rolling friction;
   wherein said sliders comprise end members coupled to the edges of said coupling plate which, along with said first, second and third pairs of guides, close a containment space of said rolling means so as to prevent impurities from entering.

2. The stacker crane according to claim 1, wherein said first, second and third pairs of guides are made with a "C"-shaped profile.

3. The stacker crane according to claim 1, wherein said first carriage and said second pair of guides are provided with a first locking mechanism, able to ensure the alignment of said movable structure with said second pair of guides, and/or said first carriage and said second carriage are provided with a second locking mechanism, able to ensure the connection of said first carriage with said second carriage.

4. The stacker crane according to claim 1, wherein said first carriage moves in said direction x along said first pair of guides driven by a first motor acting on a first pinion-rack pair, and said second carriage moves in said direction y along said second pair of guides and said third pair of guides driven by a second motor acting on a second pinion-rack pair.

5. The stacker crane according to claim 1, wherein said movable structure comprises a third carriage and said stacker crane comprises third guide means along said direction z, and
   said third carriage is able to slide integrally with said first carriage and second carriage in said direction x along said first pair of guides, integrally with said second carriage in said direction y along said second pair of guides and independently along said third guide means in said direction z, thus being released from said first carriage and from said second carriage.

6. The stacker crane according to claim 1, wherein said first guide means comprise a first pair of guides and said second guide means comprise a plurality of second pairs of guides arranged parallel side by side, so that each second pair of guides is arranged between two of said plurality of shelves facing each other.

7. The stacker crane according to claim 1, wherein said first guide means comprise a first pair of guides arranged at the same end of a plurality of said second pairs of guides.

8. The stacker crane according to claim 1, wherein said first guide means comprise a first pair of guides and said second guide means comprise a plurality of second pairs of guides arranged aligned and at the opposite ends of said first pair of guides, so that each second pair of guides is at a plurality of shelves placed side by side and separated by said first pair of guides.

9. A storage for storing containers of biological material test tubes comprising a plurality of shelves defining a plurality of locations for said containers of biological material test tubes, wherein it comprises a stacker crane for transporting, inserting and picking containers of biological material test tubes in/from locations of said plurality of shelves according to claim 1.

10. A stacker crane for transporting, inserting and picking containers of biological material test tubes in/from locations of a plurality of shelves of a storage for storing said containers of biological material test tubes, said stacker crane is able to move said containers of biological material test tubes in the three Cartesian directions x, y and z, so as to reach said locations, and comprises:
   first guide means along said direction x, comprising a first pair of guides;
   second guide means along said direction y, orthogonal to said direction x, comprising at least a second pair of guides;
   a movable structure comprising a first carriage and a second carriage, said first carriage is able to slide integrally with said second carriage in said direction x along said first pair of guides;
   wherein said second pair of guides is separate and independent from said first carriage and from said second carriage,
   said first carriage is integrally provided with a third pair of guides for said second carriage, which contribute to form said second guide means when said first carriage is arranged at said second pair of guides, thus aligning said third pair of guides to said second pair of guides,
   to each of said first carriage and second carriage is integrally connected at least one pair of sliding mechanisms located along the respective ends, and
   said second carriage is able to slide independently of, and to be released from, said first carriage along said second guide means in said direction y, by the translational movement of said sliding mechanisms of said second carriage from said third pair of guides to said second pair of guides and vice versa;
   wherein said first carriage and said second pair of guides are provided with a first locking mechanism, able to ensure the alignment of said movable structure with said second pair of guides, and/or said first carriage and said second carriage are provided with a second locking mechanism, able to ensure the connection of said first carriage with said second carriage; and
   wherein said first locking mechanism comprises a first cylinder integral with said first carriage and a housing integral with said second pair of guides, wherein said cylinder is capable of pushing a pin into said housing to ensure the alignment of said movable structure with said second pair of guides.

11. A stacker crane for transporting, inserting and picking containers of biological material test tubes in/from locations of a plurality of shelves of a storage for storing said containers of biological material test tubes, said stacker crane is able to move said containers of biological material test tubes in the three Cartesian directions x, y and z, so as to reach said locations, and comprises:
   first guide means along said direction x, comprising a first pair of guides;
   second guide means along said direction y, orthogonal to said direction x, comprising at least a second pair of guides;
   a movable structure comprising a first carriage and a second carriage, said first carriage is able to slide integrally with said second carriage in said direction x along said first pair of guides;
   wherein said second pair of guides is separate and independent from said first carriage and from said second carriage,
   said first carriage is integrally provided with a third pair of guides for said second carriage, which contribute to form said second guide means when said first carriage is arranged at said second pair of guides, thus aligning said third pair of guides to said second pair of guides,
   to each of said first carriage and second carriage is integrally connected at least one pair of sliding mechanisms located along the respective ends, and
   said second carriage is able to slide independently of, and to be released from, said first carriage along said second guide means in said direction y, by the translational movement of said sliding mechanisms of said second carriage from said third pair of guides to said second pair of guides and vice versa;
   wherein said first carriage and said second pair of guides are provided with a first locking mechanism, able to ensure the alignment of said movable structure with said second pair of guides, and/or said first carriage and said second carriage are provided with a second locking mechanism, able to ensure the connection of said first carriage with said second carriage; and
   wherein said second locking mechanism comprises a cylinder integral with said first carriage and a housing integral with said second carriage, wherein said cylinder is capable of pushing a pin into said housing to ensure the connection of said first carriage with said second carriage.

\* \* \* \* \*